US008866620B2

(12) United States Patent
Amir

(10) Patent No.: US 8,866,620 B2
(45) Date of Patent: Oct. 21, 2014

(54) SYSTEM AND METHOD FOR FALL PREVENTION AND DETECTION

(71) Applicant: Centrak, Inc., Newtown, PA (US)

(72) Inventor: Isreal Amir, Newtown, PA (US)

(73) Assignee: Centrak, Inc., Newtown, PA (US)

( * ) Notice: Subject to any disclaimer, the term of this patent is extended or adjusted under 35 U.S.C. 154(b) by 68 days.

(21) Appl. No.: 13/688,928

(22) Filed: Nov. 29, 2012

(65) Prior Publication Data

US 2014/0145848 A1    May 29, 2014

(51) Int. Cl.
*G08B 23/00* (2006.01)

(52) U.S. Cl.
USPC ..................................... 340/573.1; 340/573.7

(58) Field of Classification Search
USPC .......... 340/573.1, 573.4, 573.7, 572.1, 686.1; 600/301, 595; 607/5, 6; 73/865.4; 441/80
See application file for complete search history.

(56) References Cited

U.S. PATENT DOCUMENTS

| | | | | |
|---|---|---|---|---|
| 6,129,686 A * | 10/2000 | Friedman | | 600/595 |
| 7,974,689 B2 * | 7/2011 | Volpe et al. | | 607/6 |
| 8,284,070 B2 * | 10/2012 | Chaudhari et al. | | 340/686.1 |
| 8,613,637 B2 * | 12/2013 | Puls et al. | | 441/80 |
| 8,676,313 B2 * | 3/2014 | Volpe et al. | | 607/6 |
| 2009/0254003 A1 * | 10/2009 | Buckman | | 600/595 |
| 2011/0263950 A1 * | 10/2011 | Larson et al. | | 600/301 |
| 2012/0118084 A1 * | 5/2012 | Klose et al. | | 73/865.4 |
| 2013/0060167 A1 * | 3/2013 | Dracup et al. | | 600/595 |

* cited by examiner

*Primary Examiner* — Van T. Trieu
(74) *Attorney, Agent, or Firm* — Maldjian Law Group LLC; John Maldjian; Alexander D. Walter

(57) ABSTRACT

System and method to determine a status of a person, the method including: receiving a sensor indication of a first orientation of a first body part of the person relative to a predetermined direction; receiving a sensor indication of a second orientation of a second body part of the person relative to the predetermined direction; receiving a sensor indication of a location of the person; inferring, by use of a processor, an orientation of the person from the sensor indication of the first orientation and the sensor indication of the second orientation; and determining, by use of a processor, the status of the person from an allowability of the inferred orientation of the person at the indicated location.

24 Claims, 4 Drawing Sheets

FIG. 1
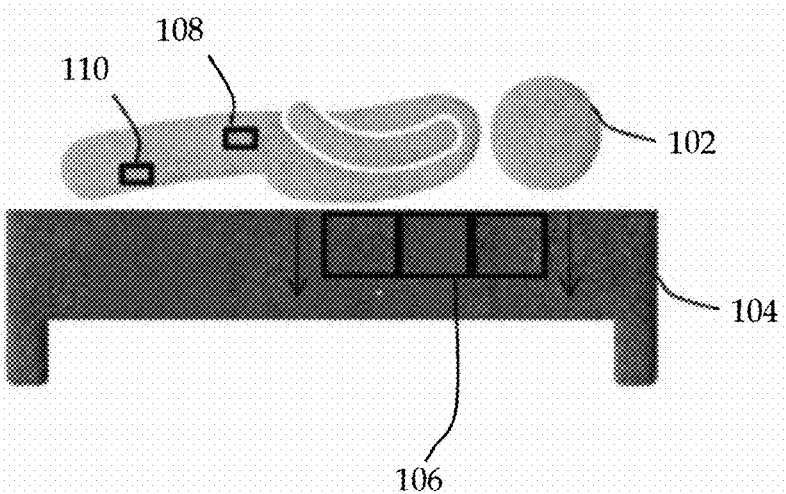
FIG. 2
FIG. 3
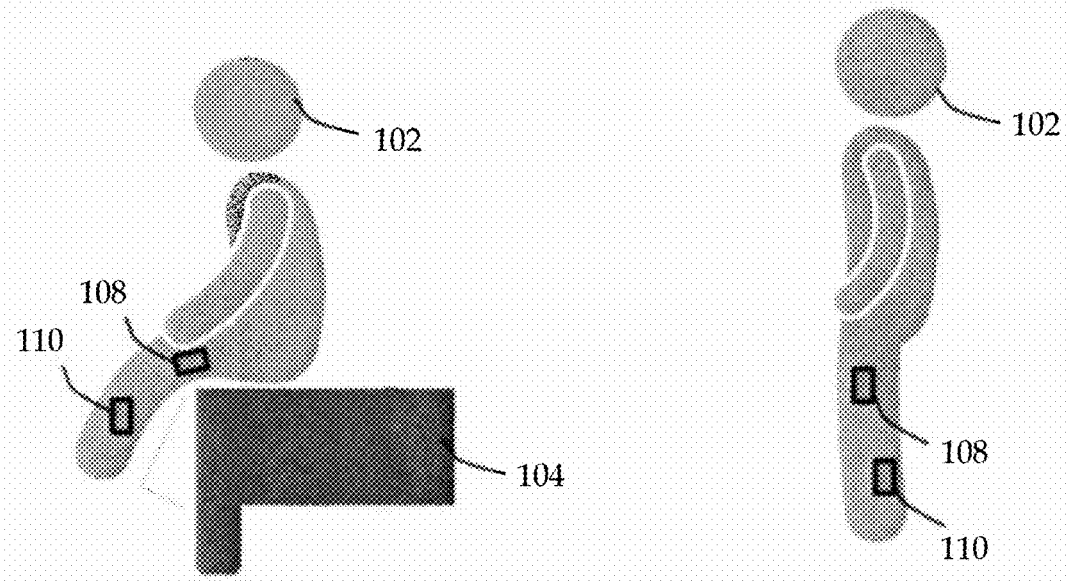

800

SYSTEM AND METHOD FOR FALL PREVENTION AND DETECTION

BACKGROUND

1. Field of the Invention

Embodiments in accordance with the present invention relate to methods and systems for fall detection and fall prevention of persons, for example elderly hospital patients. However, embodiments may be useful in for other problems, e.g., problems in which it is useful to detect that a monitored person or object is in an unexpected or unsafe physical orientation, or has been in an unchanged physical orientation for too long.

2. Description of Related Art

Certain persons such as hospital patients, and in particular elderly hospital patients, are susceptible to falls. Such persons may be weak, may have brittle bones, may have an impaired sense of balance, may have impaired judgment to avoid physically risky situations in their condition, may lack the requisite physical strength to prevent a fall and/or brace themselves during a fall, and so forth. A fall for such persons may be catastrophic and often, if not immediately fatal, can lead to quick deterioration in condition and even death. Therefore, improved systems and methods for fall prevention and detection are acutely needed.

Known systems and methods to prevent and detect falls suffer shortcomings such as a lack adequate sensitivity and an inherently high false alarm rate.

For example, one method of the known art to prevent falls is the usage of side bed rails to prevent a patient from exiting a bed unsupervised. This method is considered extremely restrictive and can cause patients to feel imprisoned. This method may have little usefulness for patients who are not confined to bed.

Another method of the known art to prevent and/or detect falls includes the usage of accelerometers to detect an impact of a patient's body with the floor. Such a method has proven to be quite poor in reliably detecting a fall for at least two reasons. First, a fall may happen with very little acceleration depending on the way the person falls and the exact position of the accelerometer on the patient body. For example, an accelerometer on a lower leg portion may be expected to experience a relatively lower acceleration during a fall as compared to an accelerometer on an upper portion of the body such as the head or shoulders. Second, an accelerometer may be susceptible to false alarms caused by, e.g., bumping a patient, bumping a bed in which a patient is laying, vibrations such as may be caused by raising or lowering the bed or portions thereof (e.g., side rails), transporting a patient in a wheelchair, elevator start/stop, and so forth. High impact of the accelerometer with substantially anything may cause high acceleration and may be difficult to differentiate from an actual fall.

Another method of the known art to prevent and/or detect falls involves using video, or a succession of still pictures, and coupled with sophisticated image processing. These methods are complex and expensive. In addition they have very limited area of coverage, e.g., just the bed and immediately adjacent area, unless an entire living area is monitored with cameras. Even with such video surveillance, the effectiveness of such methods (e.g., a probability of detection and/or a probability of false alarm) is not proven.

Another method of the known art to prevent and/or detect falls involves using a highly accurate real time location system ("RTLS") such as those based upon ultra wide band ("UWB") signals, in order to be able to detect falls based on the location of the UWB tag (e.g., height above the floor). However, UWB technology by itself is immature and relatively unreliable. Furthermore, height of the tag, by itself, is not a reliable indicator of a patient fall.

SUMMARY

In one embodiment, a method to determine a status of a person is provided, the method including: receiving a sensor indication of a first orientation of a first body part of the person relative to a predetermined direction; receiving a sensor indication of a second orientation of a second body part of the person relative to the predetermined direction; receiving a sensor indication of a location of the person; inferring, by use of a processor, an orientation of the person from the sensor indication of the first orientation and the sensor indication of the second orientation; and determining, by use of a processor, the status of the person from an allowability of the inferred orientation of the person at the indicated location.

In one embodiment, a system to determine a status of a person is provided, the system including: a first sensor coupled to a first body part of the person, the sensor configured to indicate an orientation of the first sensor relative to a predetermined direction; a location sensor configured to indicate a location of the person; a central monitor, comprising: a processor; a memory coupled to the processor, the memory comprising storage of allowable orientations of the person; a first receiver configured to receive data from the first sensor; a second receiver configured to receive data from the location sensor; an inference module configured to infer an orientation of the person from the orientation of the first sensor; and an interface to provide an alert, wherein the central interface monitor is configured to provide an alert if the allowable orientations of the person does not comprise the inferred orientation of the person.

The preceding is a simplified summary of embodiments of the disclosure to provide an understanding of some aspects of the disclosure. This summary is neither an extensive nor exhaustive overview of the disclosure and its various embodiments. It is intended neither to identify key or critical elements of the disclosure nor to delineate the scope of the disclosure but to present selected concepts of the disclosure in a simplified form as an introduction to the more detailed description presented below. As will be appreciated, other embodiments of the disclosure are possible utilizing, alone or in combination, one or more of the features set forth above or described in detail below.

BRIEF DESCRIPTION OF THE DRAWINGS

The above and still further features and advantages of the present invention will become apparent upon consideration of the following detailed description of embodiments thereof, especially when taken in conjunction with the accompanying drawings wherein like reference numerals in the various figures are utilized to designate like components, and wherein:

FIG. 1 is a diagram depicting a monitored patient reposing on a bed, in accordance with an embodiment of the present invention;

FIG. 2 is a diagram depicting a monitored patient sitting on a bed, in accordance with an embodiment of the present invention;

FIG. 3 is a diagram depicting a monitored patient standing, in accordance with an embodiment of the present invention;

Figure 4:
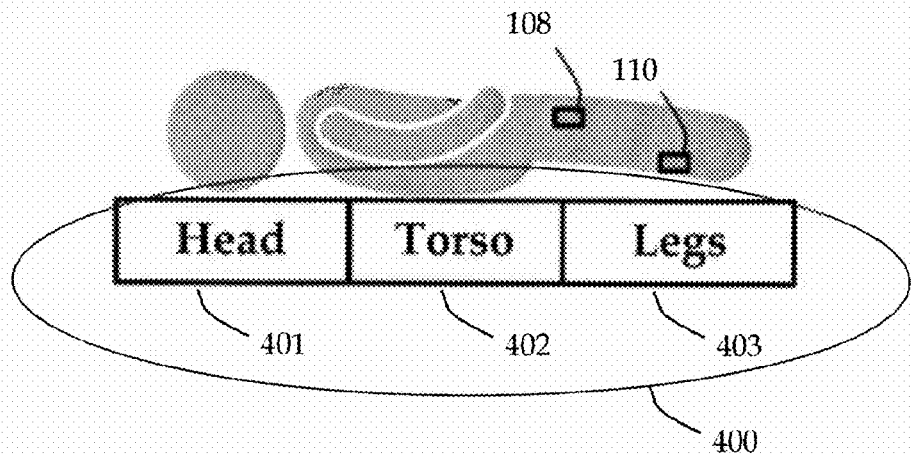
FIG. 4 is a diagram depicting a monitored patient reposing on a pressure pad, in accordance with an embodiment of the present invention.

The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include", "including", and "includes" mean including but not limited to. To facilitate understanding, like reference numerals have been used, where possible, to designate like elements common to the figures. Optional portions of the figures may be illustrated using dashed or dotted lines, unless the context of usage indicates otherwise.

DETAILED DESCRIPTION

The disclosure will be illustrated below in conjunction with an exemplary communication system. Although well suited for use with, e.g., a system using a server(s) and/or database(s), the disclosure is not limited to use with any particular type of communication system or configuration of system elements. Those skilled in the art will recognize that the disclosed techniques may be used in any communication application in which it is desirable to utilize location and/or orientation sensors that communicate with a central monitor.

The exemplary systems and methods of this disclosure may also be described in relation to software, modules, and associated hardware. However, to avoid unnecessarily obscuring the present disclosure, the following description omits well-known structures, components and devices that may be shown in block diagram form, are well known, or are otherwise summarized.

In the following detailed description, numerous specific details are set forth in order to provide a thorough understanding of embodiments or other examples described herein. In some instances, well-known methods, procedures, components and circuits have not been described in detail, so as to not obscure the following description. Further, the examples disclosed are for exemplary purposes only and other examples may be employed in lieu of, or in combination with, the examples disclosed. It should also be noted the examples presented herein should not be construed as limiting of the scope of embodiments of the present invention, as other equally effective examples are possible and likely.

As used herein, the terms "accelerometer" and "3-D accelerometer" refer generally to a device that measures the direction of acceleration and its value. A 3-D accelerometer is capable of detecting and providing the orientation of itself when at rest by use of only the force of gravity upon it. Embodiments in accordance with the present invention relate to methods that utilize this orientation-detecting feature of 3-D accelerometers.

As used herein, the term "tilt sensor" is a device that is able to provide at least an approximate indication of orientation without relying upon measurement of the direction of acceleration and its value.

As used herein, the term "Real-Time Location System (RTLS)" refers generally to a system that tracks object locations in real time, typically in an indoor environment. The position may be with respect to landmarks of the indoor environment, e.g., particular rooms, floors, building wings, and so forth. An RTLS system provides a function similar to a Global Positioning System ("GPS") for an outdoor environment. An RTLS system may also be used for tracking objects in confined areas outdoors when GPS is deemed too expensive. An exemplary RTLS system is described in U.S. Pat. No. 8,139,945, the content of which is hereby incorporated in its entirety.

As used herein, the term "RTLS tags" refers generally to typically wireless, battery operated small devices that are designed to work with an RTLS system. RTLS tags may be attached to objects (e.g., people, moveable physical assets, etc.) that need tracking. RTLS tags are typically equipped with a variety of sensors, such as sensors to improve power efficiency (e.g., a motion sensor such that processing speeds, sampling rates or the like may be increased during periods of relatively greater motion), localization (e.g., IR and Low Frequency ("LF") sensors such that communication modes may be adapted to the transmission environment), wireless radio transmitter and/or receiver in order to communicate with access points using either proprietary or standard based protocols, and so forth. For example, embodiments in accordance with the present invention may incorporate an accelerometer or orientation position sensor into the RTLS tag.

As used herein, the term "pressure pads" refers generally to pressure sensitive pads that are typically put under places a patient may be located (e.g., under patient sheets on bedding, under a chair cushion, coupled to a wheelchair, coupled to a toilet seat, etc.). Pressure pads generally have an electronic output that indicates the pressure exerted on the pad from an object on the pressure pad. Pressure pads are often used to detect the existence of patient in a bed, in a wheelchair, on a stretcher, on a toilet seat, and so forth. The lack of a significant weight on a pressure pad (e.g., beyond the weight of a cushion) may be used to infer the absence of a patient from the monitored location.

As used herein, the term "pixelized pressure pad" refers generally to a pressure pad that includes more than one individual pressure pad sensors distributed across the pressure pad in a predetermined pattern or position. For example, the pixelized pressure pad may include individual pressure pads sensors that are arranged in a rectangular pattern to form an M×N grid pattern to cover substantially the entire pixelized pressure pad.

As used herein, the term "ID beacon" or "ID beacon transmitter" in an RTLS system refers generally to a device that emits an identification ("ID") signal, usually by use of low-frequency RF signals, which can be received by corresponding receivers in tags, in order to improve localization capabilities. For example, an ID beacon transmitter may be coupled, for example, to a wheel chair, and be used to help associate a tagged patient to the wheelchair that the tagged patient is sitting in. An ID beacon transmitter generally operates by periodically transmitting its identity by use of an ID beacon signal. When a tag on a patient receives the ID beacon signal, the tag will send a transmission to a central monitoring system through access points, in order to indicate that the tag is near the ID beacon transmitter. The tag itself also has an ID, which it also transmits to the central monitoring system.

As used herein, the term "module" refers generally to a logical sequence or association of steps, processes or components. For example, a software module may comprise a set of associated routines or subroutines within a computer program. Alternatively, a module may comprise a substantially self-contained hardware device. A module may also comprise a logical set of processes irrespective of any software or hardware implementation.

As used herein, the term "transmitter" may generally comprise any device, circuit, or apparatus capable of transmitting an electrical signal.

The term "computer-readable medium" as used herein refers to any tangible storage and/or transmission medium that participates in storing and/or providing instructions to a processor for execution. Such a medium may take many forms, including but not limited to, non-volatile media, volatile media, and transmission media. Non-volatile media includes, for example, NVRAM, or magnetic or optical disks. Volatile media includes dynamic memory, such as main memory. Common forms of computer-readable media include, for example, a floppy disk, a flexible disk, hard disk, magnetic tape, or any other magnetic medium, magneto-optical medium, a CD-ROM, any other optical medium, punch cards, paper tape, any other physical medium with patterns of holes, RAM, PROM, EPROM, FLASH-EPROM, solid state medium like a memory card, any other memory chip or cartridge, a carrier wave as described hereinafter, or any other medium from which a computer can read. A digital file attachment to e-mail or other self-contained information archive or set of archives is considered a distribution medium equivalent to a tangible storage medium. When the computer-readable media is configured as a database, it is to be understood that the database may be any type of database, such as relational, hierarchical, object-oriented, and/or the like. Accordingly, the disclosure is considered to include a tangible storage medium or distribution medium and prior art-recognized equivalents and successor media, in which the software implementations of the present disclosure are stored.

Embodiments in accordance with the present invention provide a system and method for fall prevention, fall detection, and detection of a fallen state of monitored patients in a hospital. The method relies upon detection of the angular position or orientation of one or more monitored body parts (e.g., limb, torso, or portion thereof) relative to a gravitational force direction, and/or relative to another monitored body part. Embodiments may use an accelerometer to detect an orientation angle, since acceleration is ordinarily detected by a force, which may also be caused by gravity. When gravity is the source of the force, an orientation may be determined from the direction of the detected acceleration. Other embodiments may use tilt sensors. As used herein, "sensor" may refer to either an accelerometer or a tilt sensor, unless it is clear from the context that a specific type of sensor is referred to.

Embodiments in accordance with the present invention utilize a small, lightweight and attachable sensor that is able to measure its orientation with respect to either an axis, direction, plane, or three-dimensional coordinate system (e.g., with respect to the plane of the floor, or a vector direction of gravity), and thereby provide a measurement of an angle of a body part or other object to which the sensor is attached. Alternatively, the sensor may be able to measure its orientation with respect to other sensors attached to the same person or object. In contrast to at least some of the known art, a sensor in accordance with an embodiment of the present invention does not necessarily include an accelerometer that measures an impact of a fall.

The sensor is packaged in a small, lightweight package or "tag" that is intended to be affixed to a patient comfortably. The tag includes communication circuitry used to communicate with a control and monitoring system such as RTLS, a source of power (e.g., a battery), and related support circuitry. The sensor placement is important, and the sensor should be affixed to the patient at locations that provide the most useful information, i.e., the thigh, the calf, and/or the upper body.

One or more sensors if placed on a single body part may be inadequate by itself to identify with a high degree of confidence the state of a patient. For example, if one or more sensors are attached only to a patient's chest, the sensors may be able to distinguish between a patient laying down and a patient sitting up, but may be unable by itself to distinguish between a patient sitting up and a patient standing up. Similarly, a sensor placed only on a thigh may distinguish between a patient who is standing and a patient who is laying down, but may not by itself be able to distinguish between a patient laying down and a patient who is sitting. To resolve this ambiguity, multiple sensors may be used with a single patient, such that multiple separately moveable body parts may be monitored. Information from the sensors may be communicated to a monitoring system via wireless and/or infrared communication links as known in the art, such as RTLS.

In one embodiment, at least two such sensors are attached to separately moveable body parts, for example a first sensor on the leg above the knee (e.g., the thigh) and a second sensor on the leg below the knee and above the ankle (e.g., the calf or the shin). A chest-mounted sensor is also contemplated. For example, FIG. 1 illustrates a patient 102 laying on bed 104. Bed 104 is illustrated with side rails 106 in a lowered position. Patient 102 is equipped with a first sensor 108 mounted to an upper portion of a leg of patient 102, and a second sensor 110 mounted to a lower portion of the leg of patient 102.

The sensors 108, 110 should be placed on the same leg, but may be placed on different legs if for some reason (e.g., location of wounds, bandages, etc.) they cannot be placed on the same leg. The two sensors should not be placed on body parts that, although separately moveable, would be expected to usually be in the same orientation. For example, if a first sensor is on a left thigh, the second sensor should not be on the right thigh. Sensors placed on different legs may be susceptible to conflicting indications if the patient moves their legs independently. The sensors should be attached to the body part such that the sensor cannot substantially move independently of the body part, yet the sensor is attached in a manner that is comfortable to the patient. Alternatively, the sensor may be attached to an apparatus (e.g., a cast, a brace, etc.) which in turn is rigidly attached to the desired portion of the patient's body. The sensors should be oriented on the patient such that a major axis of the sensor, which indicates upright vertical orientation of the sensor, should be aligned substantially parallel to the major bone in that portion of the leg, and pointed toward the upper end of the bone. In this embodiment, a patient state includes the relative angle between the calves, the shin and the center of the earth (as determined by the direction of the force of gravity). A vertical direction is parallel to the force of gravity, and a horizontal direction is perpendicular to the force of gravity.

Embodiments in accordance with the present invention measure the orientation of the first and second sensors (e.g., on the calf and on the thigh), either relative to each other or relative to an axis, direction, plane, or three-dimensional coordinate system, is measured. In particular, the angle between a vertical axis and the major axis of the sensor in its present orientation may be measured. Some embodiments may estimate whether the patient is sitting, laying down or standing up by using the sensor measurements. The sensors may be able to distinguish between one position and position rotated 180° from that position. For example, the sensor may be able to distinguish between a patient who is standing up and one who is laying in bed but who has lifted their leg upward into a vertical position.

For example, FIG. 2 illustrates orientation of sensors 108, 110 when patient 102 is sitting, such as on an edge of bed 104. Sensor 108 may be substantially horizontal, and sensor 110 may be substantially vertical. FIG. 3 illustrates orientation of sensors 108, 110 when patient 102 is standing, in which sensors 108, 110 both may be substantially vertical.

Table 1 below lists various inferences about the state of the patient that may be inferred based upon the orientation of the calf and thigh sensors. Persons of skill in the art will be able to extend Table 1 to include sensors placed on other body parts such as the chest. It should be understood that there is a tolerance (e.g., approximately 20°) when determining the state of the sensors due to factors such as the actual placement of the tag on the patient, patient joint mobility, etc.

TABLE 1

| Calf state | Thigh state | Inference |
| --- | --- | --- |
| Horizontal | Horizontal | Laying down |
| 45° to vertical | 45° to vertical | Knees raised, feet flat on bed |
| Horizontal | Inverted vertical | Knees raised, feet held out |
| Inverted vertical | Inverted vertical | In bed, legs fully raised |
| Vertical | Horizontal | Sitting |
| Vertical | Vertical | Standing |
| Vertical | Unknown | Standing or sitting, but not laying |
| Horizontal | Unknown | Laying or knees raised with feet held out, but not sitting or standing |
| Unknown | Vertical | Standing |
| Unknown | Horizontal | Sitting or laying, but not standing |

In one embodiment of the invention, a fall-prevention process and system is disclosed, which infers various different states of a patient, based upon sensor measurements and, optionally, based upon identification of permitted or prohibited actions for a patient. The tag may include an accelerometer and an embedded wireless transmitter, which periodically communicates the acceleration measurements to a central monitoring system, so that the central monitoring system can activate alerts when needed. In yet another embodiment the accelerometer may be embedded within an RTLS tag. The central monitoring system may be configured to receive and process sensor measurements from a plurality of patients, such as patients throughout a hospital or sections thereof. A processor in the central monitoring system may calculate an inference of patient state from the reported sensor orientations. The processor may compare the inferred patient state or position against a list of safe states (i.e., allowed states) and/or a succession of states for that patient, the safe states or safe succession of states having been provisioned and stored in a database or other memory coupled to the central monitoring system. A repetition rate for determining the patient state may adaptively change based on predetermined factors (e.g., time of day, patient activity during the previous X number of seconds, etc.). The repetition rate may change between, e.g., several times per second during the day, to several seconds between measurements while the patient is sleeping, in order to conserve system resources such as battery power in the tag, processing power in the central monitoring system, and so forth. An alarm may be raised and/or repetition rate increased if the patient is inferred to be in an unsafe (i.e., unallowed) state.

In particular, sitting is a dangerous state if the patient is sitting in an unsafe location, such as on the side of their bed or a stretcher, because this may indicate that the patient will try to stand. Getting out of bed may be unsafe (i.e., there is a higher likelihood of a fall by the patient) because the bed or stretcher surface is often elevated compared to places a patient may safely sit. However, without more information, there may exist ambiguity whether a patient is dangerously sitting on the side of a bed or stretcher, or is safely sitting somewhere else such as a chair, wheelchair, toilet seat, etc. Furthermore, a "laying down" inference by itself is not adequate to distinguish between a safe state (e.g., laying in bed or a stretcher) or an unsafe state (e.g., laying on the floor after a fall).

Alternatively, information from a single sensor may be correlated with or compared to information derived from or provided by other systems. For example, although a chest-mounted sensor by itself may be unable to distinguish between a patient sitting up and a patient standing up, either state would raise an alarm if either the patient is not allowed to get out of bed or if other non-patient mounted sensors could detect that the patient is not in bed.

Therefore, embodiments in accordance with the present invention may resolve this ambiguity by using an appropriate sensor coupled to the patient's bed or stretcher. For example, an appropriate sensor may be a pressure sensor. The pressure sensor may include a pressure-sensitive pad on top of the mattress (e.g., under a sheet) in order to detect the weight of the patient. The pressure sensor may also be placed in other locations, such as integrated into the mattress, or under the bed if there is sufficient resolution to distinguish between the weight of the bed with a patient compared to the bed by itself. A "sitting" inference while such a sensor indicates pressure may cause an alarm, and a "laying" inference without an indication of pressure from such a sensor may cause an alarm.

In yet another embodiment of the current invention the pressure sensor pad may be "pixelized." Such pixelized pressure pads may include a plurality of individual pressure sensors (i.e., "pressure pixel"), each of which measures the pressure in a predefined portion of a larger surface such as the patient's bed. FIG. 4 illustrates an example of a pixelized pressure pad 400, in which a pressure sensor pad has been divided into three sections or pressure pixels 401, 402, 403. Pixelized pressure pad 400 may be used to infer that, e.g., a patient may be laying in bed because of high pressure measured in central pressure pixel 402 and lesser but still high pressure on outer or edge pressure pixels 401, 403, or that a patient may be sitting on the bed because of an even higher pressure (compared to the laying scenario) measured in central pressure pixel 402 and little or no pressure on outer or edge pressure pixels 401, 403. An expected map of pressures for a predetermined patient may be stored by a central monitoring system.

Pixelized pressure pads may be used to monitor an activity level of the patient. A map of the pressure exerted on the pad may be recorded continuously, such that an analysis of the pressure map data provides a state of the patient. Dynamic measurements from the pixelized pressure pads, or calculations based upon the dynamic measurements, may include identification of which individual pressure sensors measure (or do not measure) an expected level of pressure, a change in the pressure measurements over time, a relationship (e.g., a ratio) between adjacent or otherwise related individual pressure sensors, repetitiveness, frequency of changes, and so forth. The dynamic measurements may be used to indicate or to infer a level of agitation by the patient, and thereby inferring an intent by the patient to get out of bed. For example, a rapid redistribution of pressure measurements across the pad may indicate patient agitation, which is predictive of a will of a patient to get out of bed.

Alternatively, the pressure pad may be located where patients may safely sit. For example, a "sitting" inference while such a sensor indicates pressure from the patient may not be cause for alarm. However, such locations for pressure sensors are susceptible to measuring the weight of other people or objects, such as visitors sitting in a chair or objects placed on the chair.

Figure 5:
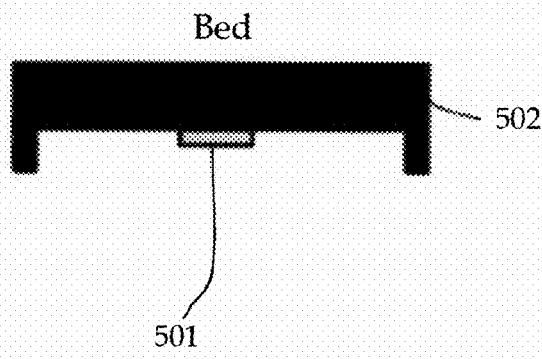
FIG. 5 illustrates an ID beacon transmitter coupled to a bed, in accordance with an embodiment of the present invention.
Figure 6:
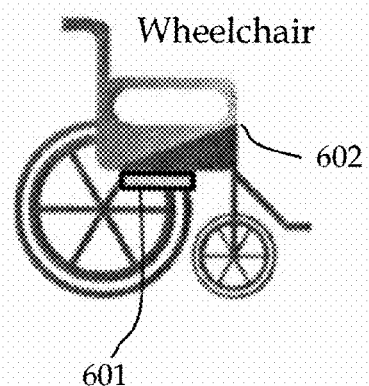
FIG. 6 illustrates an ID beacon transmitter coupled to a wheelchair, in accordance with an embodiment of the present invention.
Figure 7:
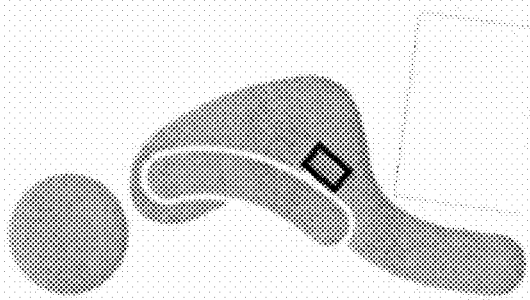
FIG. 7 is a diagram depicting a monitored patient after a fall, in accordance with an embodiment of the present invention.

In another embodiment in accordance with the present invention, one or more pressure pads may be used in beds, wheel chairs, stretchers, toilet seats, and other places that a patient may use or have access to. An association of patients to wheelchairs can be made, for example, by assignment, by using RTLS, or by using one or more ID beacon transmitters together with a tag on the patient. An ID beacon transmitter may operate by transmitting its ID using a low frequency signal (e.g., approximately 125 KHz center frequency). At such frequencies the ID beacon transmitter can establish a well defined bubble around itself, with a range of up to 10 to 20 feet, with predictable transmission characteristics and negligible multipath effects. For example, FIG. 5 depicts ID beacon transmitter 501 coupled to bed 502, and FIG. 6 depicts ID beacon transmitter 601 coupled to wheelchair 602. A database in a central monitoring system may store allowable patient states with respect to information from ID beacon transmitters and/or one or more tags on the patient, e.g., whether a patient is allowed to be in a laying position only when the patient is in bed or on a stretcher, and allowed to be in a sitting position only in wheelchairs and on toilets. Anywhere else such positions will trigger an alert. For example, FIG. 7 illustrates a patient laying on a floor, which would trigger an alert. In one embodiment of this invention the position sensors and the RTLS tag may be combined into a single physical device.

Alternatively, RTLS can be used to track the patient location. The pressure pads together with an ability to associate a patient with a moving platform such as wheelchairs and stretchers provides a comprehensive status, including patient location and orientation, needed for reliable indication of the patient status. Moving platforms (e.g., wheelchair, stretcher) may utilize battery-operated sensors coupled to the moving platforms. The RTLS tag on the patient will associates the patient with the moving platform that the patient is on.

Angle measurement using accelerometers as well as tilt sensors are sensitive to "dynamic" accelerations other than gravity. For example, a patient being moved may experience such dynamic accelerations while moving in a wheelchair or stretcher, on an elevator, etc. Therefore, some embodiments in accordance with the present invention utilize secondary processing of the sensor measurements in order to substantially filter out the measurements due to dynamic accelerations, leaving substantially only the measurements due to gravity acceleration forces. In one embodiment of secondary processing, filtering is done by accepting only substantially similar consecutive acceleration results (e.g., consecutive measurements that are within a configurable tolerance of each other), which is indicative of a constant gravitational force. Dynamic accelerations are expected to be variable in nature, and measurements exhibiting such variation will be ignored.

In yet another embodiment of the current invention, the position sensor may be used to monitor a patient and provide an alert signal if the patient or a major body part of the patient (e.g., torso or a limb) is in a substantially still position for more than a predetermined amount of time (e.g., two hours) before the patient needs to be moved or rolled over to prevent sores from forming. Alternatively, information about patient movement or lack of movement may be provided by, e.g., a pressure sensor pad incorporated into bedding, chairs, or the like. The predetermined amount of time may depend upon time of day, for example, a longer time may be allowed during the night.

Figure 8:
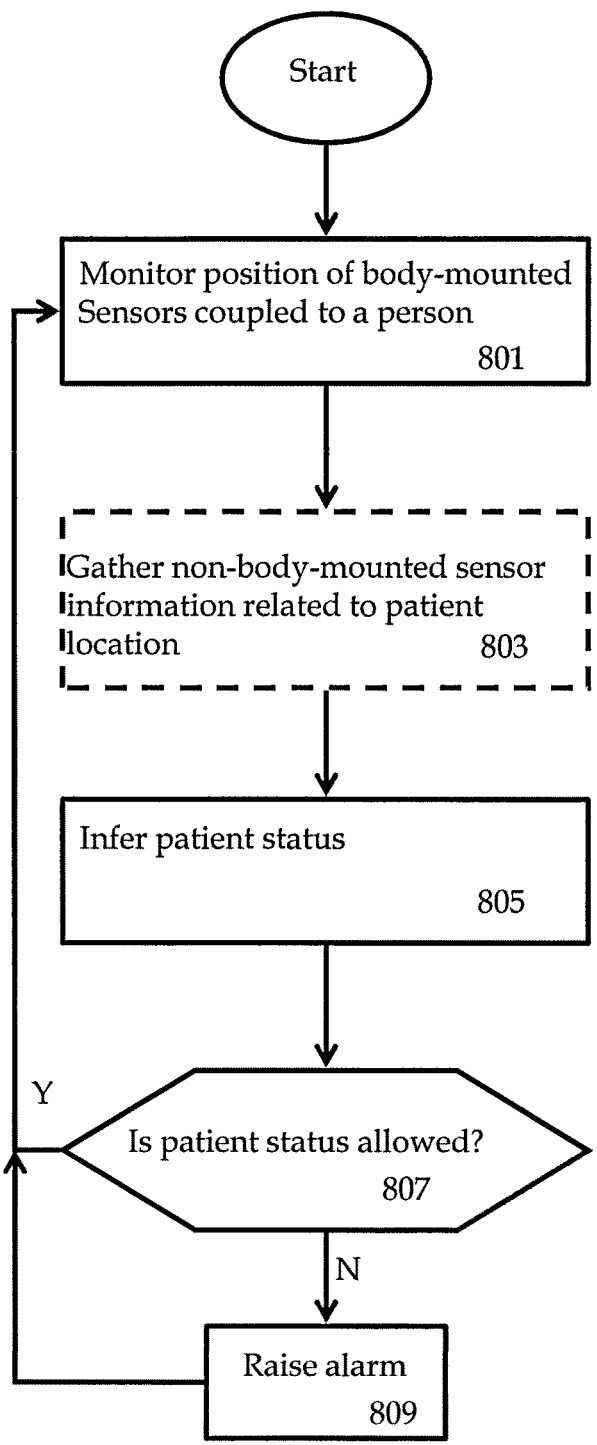
FIG. 8 illustrates at a high level of abstraction a process to monitor a patient, in accordance with an embodiment of the present invention.

FIG. 8 illustrates at a high level of abstraction a process 800 to monitor a patient status in accordance with an embodiment of the present invention. Process 800 begins at step 801, at which the position of one or more body-mounted sensors (or sensors mounted to an apparatus which in turn is affixed to a patient) relative to a predetermined direction, such as an axis, direction, plane, or three-dimensional coordinate system, or relative to each other, is detected, measured, or otherwise monitored. Sensors as described herein may be used by process 800. The sensors will be attached to body parts of a patient in order to provide information about the orientation of the patient's monitored body parts.

Next, at step 803, non-body-mounted sensor information may optionally be gathered. For example, types of data that may be gathered include pressure data from a pixelized pressure pad, pressure sensors that monitor places a patient may be sitting (e.g., chair, toilet seat, etc.), sensors that indicate a location of the patient, LF sensors, and so forth.

Next, at step 805, patient status is inferred from the information provided by the body-mounted sensors and (if available) the non-body-mounted sensors. The information may be provided to a central monitoring system, which in turn makes the inference about patient status from the information.

Next, at step 807, is a decision step to determine whether the patient status is an allowable status. For example, if a patient is supposed to be confined to bed, then a status indicating an upright position is not safe. Or, if body-mounted sensors indicate that a patient is in a prone (i.e., horizontal) position but non-body-mounted sensors indicate that the patient is not in a bed or stretcher, then the patient is in an unsafe state. If the result of decision step 807 is that the patient is in a safe state, then control of method 800 loops back to step 801, at which monitoring continues. If the result of decision step 807 is that the patient is not in a safe state, then control of method 800 passes to step 809 at which an alarm is raised. At the conclusion of step 809, control of method 800 loops back to step 801, at which monitoring continues.

The disclosed methods may be readily implemented in software, such as by using object or object-oriented software development environments that provide portable source code that can be used on a variety of computer or workstation platforms. Alternatively, the disclosed system may be implemented partially or fully in hardware, such as by using standard logic circuits or VLSI design. Whether software or hardware may be used to implement the systems in accordance with various embodiments of the present invention may be dependent on various considerations, such as the speed or efficiency requirements of the system, the particular function, and the particular software or hardware systems being utilized.

While the foregoing is directed to embodiments of the present invention, other and further embodiments of the present invention may be devised without departing from the basic scope thereof. It is understood that various embodiments described herein may be utilized in combination with any other embodiment described, without departing from the scope contained herein. Further, the foregoing description is not intended to be exhaustive or to limit the invention to the precise form disclosed. Modifications and variations are possible in light of the above teachings or may be acquired from practice of the invention. Certain exemplary embodiments may be identified by use of an open-ended list that includes wording to indicate that the list items are representative of the embodiments and that the list is not intended to represent a closed list exclusive of further embodiments. Such wording may include "e.g.," "etc.," "such as," "for example," "and so forth," "and the like," etc., and other wording as will be apparent from the surrounding context.

No element, act, or instruction used in the description of the present application should be construed as critical or essential to the invention unless explicitly described as such. Also, as used herein, the article "a" is intended to include one or more items. Where only one item is intended, the term "one" or similar language is used. Further, the terms "any of" followed by a listing of a plurality of items and/or a plurality of categories of items, as used herein, are intended to include "any of," "any combination of," "any multiple of," and/or "any combination of multiples of" the items and/or the categories of items, individually or in conjunction with other items and/or other categories of items.

Moreover, the claims should not be read as limited to the described order or elements unless stated to that effect. In addition, use of the term "means" in any claim is intended to invoke 35 U.S.C. §112, ¶6, and any claim without the word "means" is not so intended.

What is claimed is:

1. A method to determine a status of a person, comprising the steps of:
   receiving an indication from a first sensor, of a first orientation of a first body part of the person relative to a predetermined direction;
   receiving an indication from a second sensor, of a second orientation of a second body part of the person relative to the predetermined direction, wherein the second body part is separately moveable from the first body part;
   inferring, by use of a processor, an orientation of the person from the indication from the first sensor of the first orientation and the indication from the second sensor of the second orientation; and
   determining, by use of a processor, the status of the person from an allowability of the inferred orientation of the person.

2. The method of claim 1, wherein the status of the person comprises one of a fallen state and a likelihood of a fall.

3. The method of claim 1, further comprising the step of receiving a sensor indication of a location of the person.

4. The method of claim 3, further comprising the step of determining, by use of a processor, the status of the person from the indicated location.

5. The method of claim 3, wherein the sensor indication of the location of the person is provided by a pressure pad.

6. The method of claim 5, wherein a location of the pressure pad comprises one of a bed, a wheelchair, a stretcher and a toilet seat.

7. The method of claim 6, further comprising the step of associating the person with the pressure pad by use of an ID beacon transmitter.

8. The method of claim 5 wherein the pressure pad comprises a plurality of pressure pad sensors configured to provide an indication of temporal pressure variation across the pressure pad.

9. The method of claim 8, further comprising the step of analyzing the temporal pressure variation to detect rapid movements, wherein rapid movements indicate an agitated person condition.

10. The method of claim 3, wherein the location of the person is determined by a real-time location system.

11. The method of claim 1, wherein the first body part comprises a thigh.

12. The method of claim 1, wherein the first body part comprises a portion of a leg below a knee.

13. The method of claim 1, further comprising the step of inferring a sitting status of the person when the first orientation is horizontal and the second orientation is vertical.

14. The method of claim 1, wherein the indication of a first orientation is provided by a 3-D accelerometer.

15. The method of claim 1, wherein the indication of a first orientation is provided by a tilt sensor.

16. The method of claim 1, wherein the status of the person comprises whether a major body part of the person is in a substantially same orientation for more than a predetermined amount of time.

17. The method of claim 1, wherein the first sensor is attached to the first body part such that the first sensor cannot substantially move independently of the first body part, and wherein the second sensor is attached to the second body part such that the second sensor cannot substantially move independently of the second body part.

18. The method of claim 1, wherein the status of the person is independent of time spent by the person in the inferred orientation.

19. A system to determine a status of a person, comprising:
   a first sensor coupled to a first body part of the person, the sensor configured to indicate an orientation of the first sensor relative to a predetermined direction;
   a second sensor coupled to a second body part of the person, the second sensor configured to indicate an orientation of the second sensor relative to a predetermined direction, wherein the second body part is separately moveable from the first body part;
   a central monitor, comprising:
      a processor;
      a memory coupled to the processor, the memory comprising storage of allowable orientations of the person;
      a first receiver configured to receive data from the first sensor;
      a second receiver configured to receive data from the second sensor;
      an inference module configured to infer an orientation of the person from the orientation of the first sensor and the orientation of the second sensor; and
      an interface to provide an alert,
   wherein the central interface monitor is configured to provide an alert if the allowable orientations of the person does not comprise the inferred orientation of the person.

20. The system of claim 19, further comprising:
   a location sensor configured to indicate a location of the person, and
   wherein the central monitor further comprises a second receiver configured to receive data from the location sensor.

21. The system of claim 19, wherein the location sensor comprises a pixelized pressure pad.

22. The system of claim 19, wherein the first sensor comprises a 3-D accelerometer.

23. The system of claim 19, wherein the first sensor comprises a tilt sensor.

24. The system of claim 19, wherein the inference module is further configured to infer an orientation of the person from the orientation of the second sensor.

* * * * *

UNITED STATES PATENT AND TRADEMARK OFFICE
CERTIFICATE OF CORRECTION

| | | |
|---|---|---|
| PATENT NO. | : 8,866,620 B2 | Page 1 of 1 |
| APPLICATION NO. | : 13/688928 | |
| DATED | : October 21, 2014 | |
| INVENTOR(S) | : Israel Amir | |

It is certified that error appears in the above-identified patent and that said Letters Patent is hereby corrected as shown below:

On the title page, Item 72

Inventor: "Isreal Amir, Newtown, PA (US)" should read -- Israel Amir, Newtown, PA (US) --

Signed and Sealed this
Fifteenth Day of March, 2016

Michelle K. Lee
*Director of the United States Patent and Trademark Office*